United States Patent

Hocking et al.

[11] 3,931,571
[45] Jan. 6, 1976

[54] EDDY CURRENT METAL SURFACE FLAW DETECTOR

[75] Inventors: Donald Henry Hocking, St. Albans; John Henry Calvert, Hatfield; Richard Dennis, Bushey Heath, all of England

[73] Assignee: Hocking Associates (Electronics) Limited, England

[22] Filed: June 14, 1974

[21] Appl. No.: 480,136

[30] Foreign Application Priority Data
Aug. 21, 1973 United Kingdom............ 39488/73

[52] U.S. Cl. ............................................. 324/37
[51] Int. Cl.² .................................... G01R 33/12
[58] Field of Search ......................... 324/37, 40

[56] References Cited
UNITED STATES PATENTS

| | | | |
|---|---|---|---|
| 2,928,043 | 3/1960 | Foerster | 324/37 |
| 3,723,861 | 3/1973 | Samples | 324/40 |

FOREIGN PATENTS OR APPLICATIONS

| | | | |
|---|---|---|---|
| 624,719 | 8/1961 | Canada | 324/37 |
| 870,487 | 6/1961 | United Kingdom | 324/37 |

Primary Examiner—Robert J. Corcoran
Attorney, Agent, or Firm—Young & Thompson

[57] ABSTRACT

A flaw detecting device responding to variations in eddy currents induced in a surface under test includes an oscillatory circuit comprising a tuned detector circuit including a detector coil. The detector circuit is in series with an inductor and preferably capacitors are in parallel with the detector coil and with the detector coil and inductor respectively. The oscillatory circuit includes also a two stage amplifier with zero phase shift and a capacitor between the output of the amplifier and earth. The oscillatory circuit operates to successively decrease its output amplitude when the detector is moved from free air to adjacent a flawless surface and then adjacent a flaw in the surface.

11 Claims, 7 Drawing Figures

EDDY CURRENT METAL SURFACE FLAW DETECTOR

This invention relates to detectors for flaws in metal, and more especially eddy current detectors for cracks in or near to the surface of a metal object.

The invention consists in a device for detecting flaws in metal comprising means for establishing an oscillatory electromagnetic field, and for exploring a metal surface by moving said field adjacent to said surface, means adapted to detect a variation of reaction between said field and the metal surface over which it is moved, arising from a flaw, such as a crack or other discontinuity, in said metal surface, and to provide a signal which is substantially in linear proportion to a dimension of said flaw, for the purpose of actuating indicating or measuring means to identify the flaw.

The exploration may be effected by an instrument incorporating a small tuned electric circuit driven by a finely-tuned oscillatory circuit. The oscillatory circuit may be adapted to be preset when the exploratory means are associated with a flawless metal standard. The indicating or measuring signal may be obtained by integration technique to sum small variations of the individual oscillations over a short period of time. A discrimination circuit may be incorporated to block passage of a signal unless it exceeds a pre-arranged value (which may be adjustable).

The invention will be clearly understood from the following description of one form, (given, however, merely by way of example) which it may assume, and this description will be more readily followed by reference to the accompanying drawings wherein FIG. 1 represents in perspective a probe for surface exploration of a metal object when incorporated in a detector in accordance with the invention;

Figure 7:
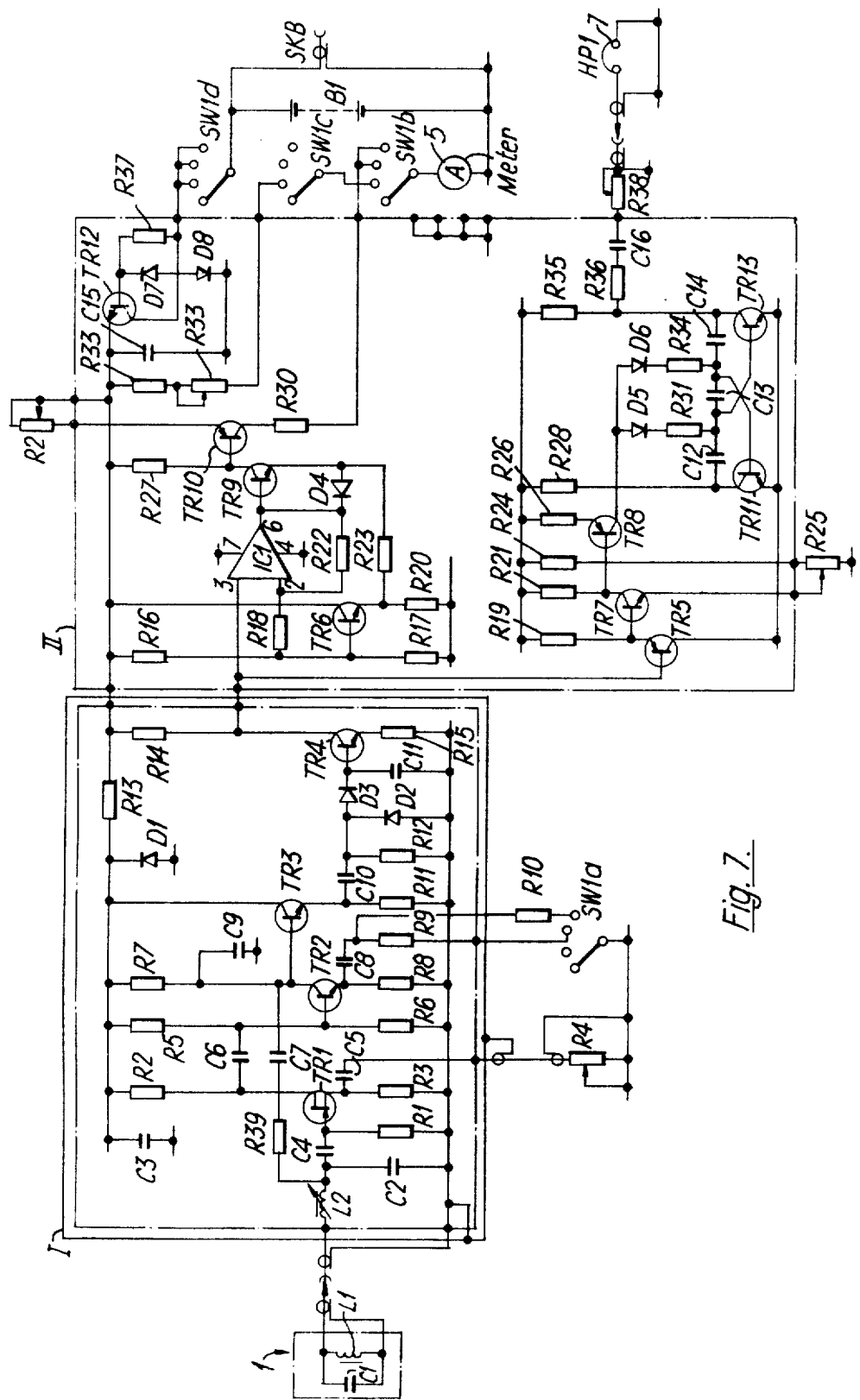

FIG. 7 provides full circuit details of a detector in accordance with the invention.

In carrying the invention into effect in one convenient manner, as shown in the aforesaid drawings, a detector for locating flaws, and more especially cracks, in a metal object comprises a detector 1 (FIGS. 1–3) driven by a tuned oscillator 2 (FIG. 2), a converter 3 functioning to integrate variations of the signal received from the oscillator 2, and to exercise discrimination in respect thereof, and an amplifier 4 feeding flaw-indication or measuring signals to a display device 5. Provision may also be made for signals from the converter 3 to be fed to an audio generator 6 to enable an operator to detect signal changes due to detected flaws by means of earphones 7 or the like.

Figure 3:
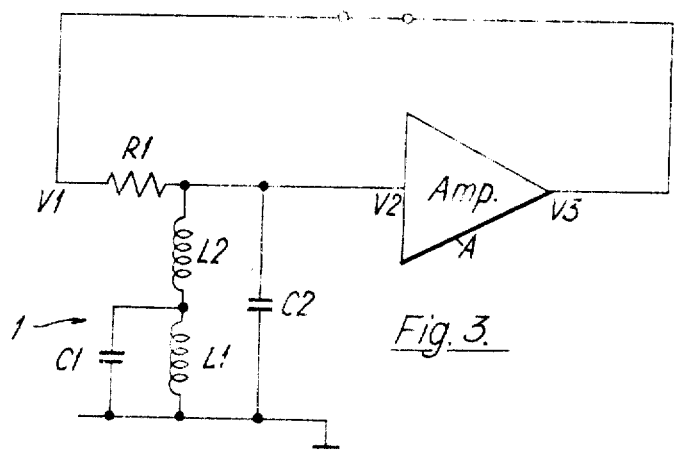
FIG. 3 represents details of the tuned circuit used for investigation.

The detector may be in the form of a manually-operable probe comprising a tubular casing 8 (FIG. 1) in which at its tip is mounted a coil L1 wound on a ferrite core 9, in circuit with a capacitor C1 housed inside the casing, the casing being formed with a handle 10 through which pass leads for connection to the main circuit unit, in which, by way of a variable inductance L2 and a capacitor C2 it is connected to an amplifier A (FIG. 3).

Figure 1:
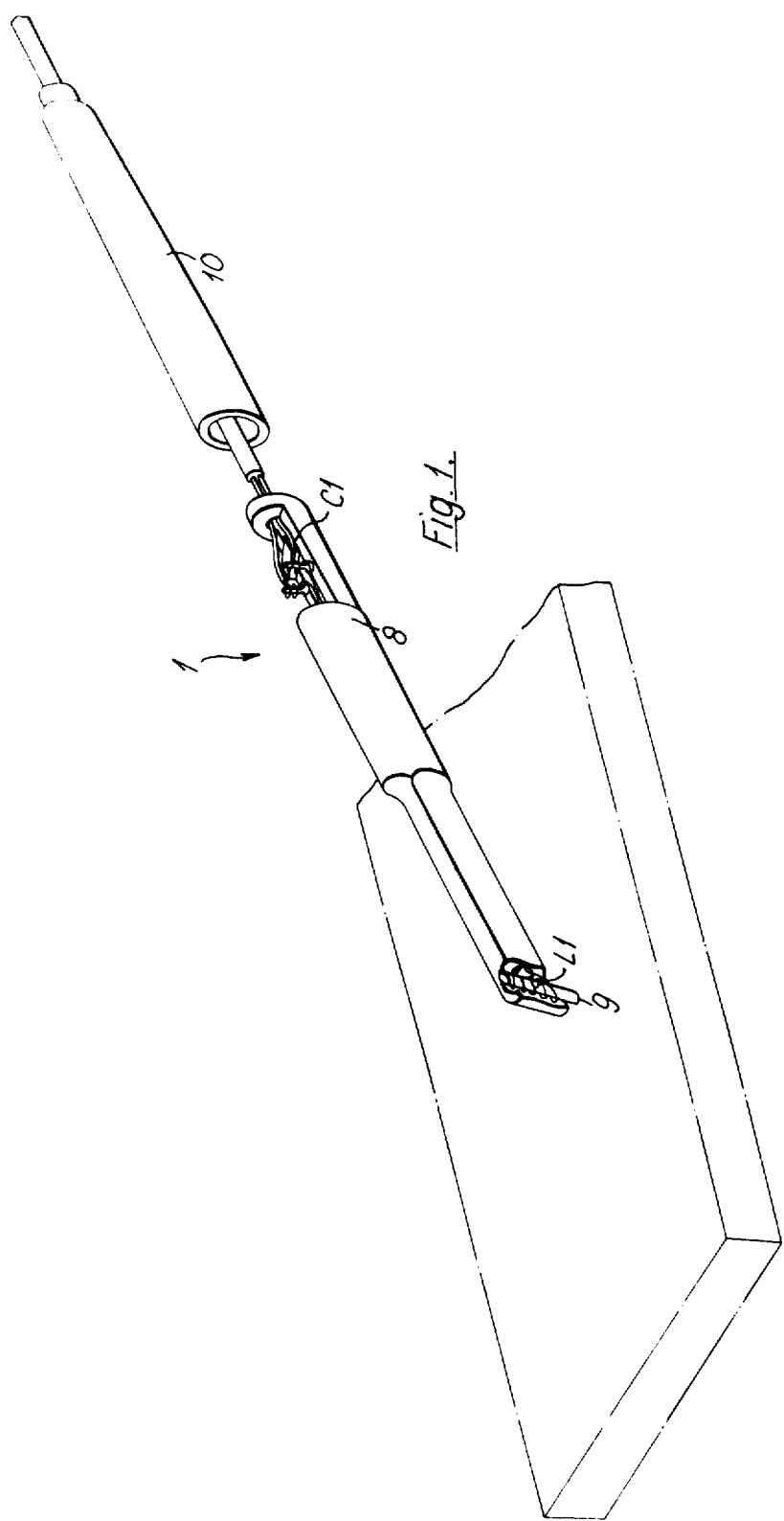
Figure 2:
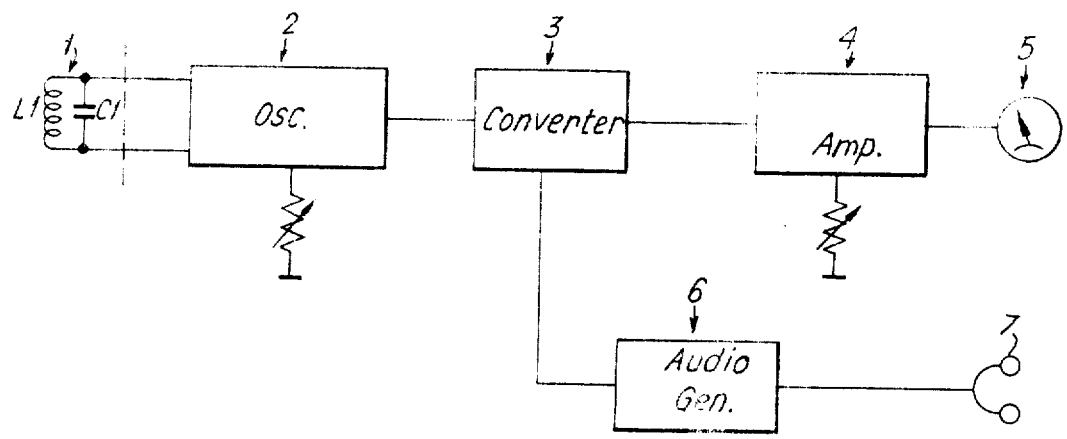
FIG. 2 represents a block circuit diagram of a detector in accordance with the invention.

The mode of operation of a detector in accordance with the invention will be appreciated by reference to FIGS. 1–3.

Alternating current generated by the oscillator 2 drives the tuned circuit of the probe 1, and the latter, located adjacent to a metal surface (FIG. 1) generates eddy currents in the metal which react with the electromagnetic field established by the probe. The strength of the field set up by the eddy currents depends inter alia upon the conductivity of the metal, and also upon continuity or homogeneity of the metal in the vicinity of the probe. If, therefore, as the probe traverses the metal surface the coil L1 comes into the vicinity of a discontinuity, such as a crack, in the adjacent metal the action of the eddy currents on the field of the probe is modified, (e.g. causes a change of amplitude and frequency of an output signal) and this variation is employed to locate and measure the flaw.

Initially the oscillator is adjusted, while the probe is applied to a sound, unflawed, metal object of similar character to the object being investigated, in order to compensate for differing surface conductivities and the like, and the sample under test is thereafter superficially explored by traversing the probe over its surface.

When the probe rides over a crack the output signal from the amplifier A is modified in both amplitude and frequency. Since the variation in amplitude of the individual oscillations of the signal is small, an integration technique is employed to provide a summation of variation of individual oscillations over a short period of time, and the output from the summation circuit (which may incorporate an amplifier having a pre-arranged gain factor) is fed to a discrimination circuit in the converter 3, in which the gain factor is adjustable. The function of this discrimination circuit is to compare the value of voltage of the incoming signal with a pre-set voltage in order to determine the difference. As long as the incoming signal voltage is less than the pre-set value, no signal is passed to the meter 5, but when the incoming signal voltage exceeds the pre-set value, the difference, after amplification in the amplifier 4, is fed to the meter 5 causing a deflection thereof proportioned to the difference between the two voltages. The circuit is designed to ensure linear proportionality of the signals passed through successive stages, to ensure that when the circuit is correctly set initially, the meter reading is directly proportional to the depth of a crack, at least for a simple, unbranched, tight crack, (although factors such as branching and different width-to-depth ratios in cracks may, as usual, affect linearity of readings to some extent).

If it is desired also to provide an audio facility in the apparatus an output from the summation circuit amplifier may be fed from the converter 3 to an audio generator 6 which comprises an amplifier incorporating a threshold control passing a signal to a voltage-to-frequency converter. This circuit provides for the headphones 7 a signal at an audible frequency which varies in accordance with variation of the voltage from the threshold control, and in linear relation thereto, from zero when the voltage applied to the amplifier reaches the threshold value, to frequencies increasing in direct proportion to excess value of the applied voltage above the threshold value. Thus the frequency of the audio signal is in linear relation to the depth of a crack located by the probe. The sensitivity of the circuit (in proportion to the ratio of the inductive coils L1 and L2, FIG. 3) can be increased by increasing the inductance of coil L1.

Figure 4:
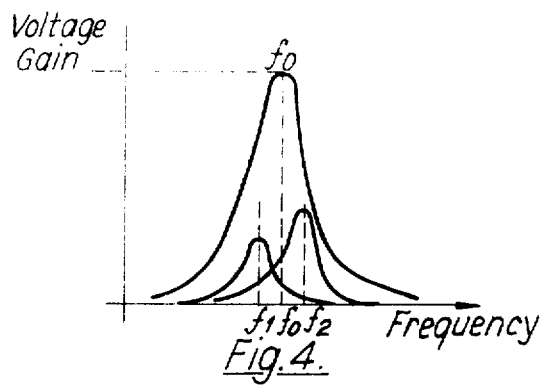
FIGS. 4, 5 and 6 represent circuit characteristics of the apparatus in use.

The characteristics of the tuned circuit under different conditions are illustrated in FIG. 4 representing voltage gain (V2/V1 in FIG. 3) as ordinate values for varying applied frequencies as abscissa, of a probe in accordance with the invention. When the probe circuit is set into oscillation in free air it supplies an output of maximum gain at a resonant frequency $f0$. When the probe is applied to an uncracked metal surface the "Q" reduces and the gain is reduced, and the resonant frequency increases to a value $f2$. If in traversing the metal surface the probe identifies a crack the "Q" is still further reduced, and the resonant frequency falls to a value $f1$ below $f2$, but not necessarily below $f0$.

Figure 5:
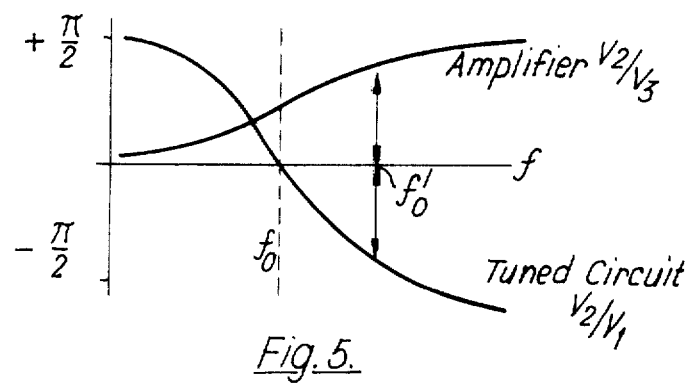

The phase characteristics of the amplifier and tuned circuit are represented in FIG. 5 showing phase as ordinate in relation to frequency as abscissa. It can be seen that the condition for oscillation which occurs when the overall phase shift between V1 and V3 (FIG. 3) is zero is established at a frequency $f0'$, which is higher than the resonant frequency $f0$ of the tuning circuit.

Figure 6:
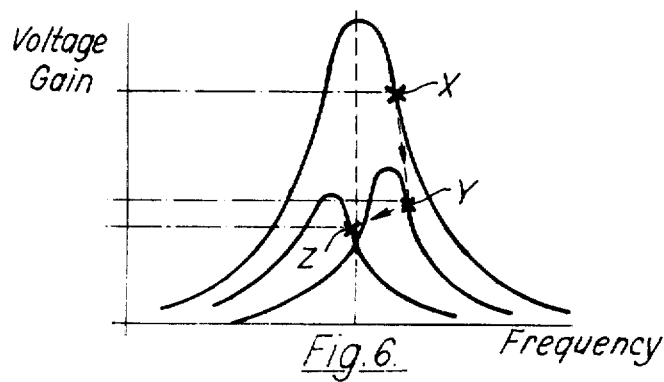

The resultant functioning of the circuit can be seen from FIG. 6, where the operating point moves from X when the tuning circuit is in free air, to Y when the tuning circuit is adjacent to an unflawed metal surface, and to Z when the tuning circuit traces a crack, and when the amplitude of the oscillator output voltage falls to a low value.

The complete circuit diagram of a crack detector in accordance with the invention is shown in FIG. 7, where the components (shown as mounted on two boards I and II) are represented by symbols laid down in British Standards Leaflet No. 3939. The oscillatory circuit L1, C1, and L2, C2 is connected to an amplifier having two stages TR1 and TR2—(corresponding to the amplifier A shown in FIG. 3), with adjustable gain to allow initial setting up of the probe. The circuit incorporates components R9 and R10, which can be included in, or excluded from, the circuit. Each in association with components R7, R8 and C9 constitute fixed gain components to set the device for variations between ferrous and non-ferrous specimens under test. A continuously variable gain component R4 may also be provided to allow adjustment for varying individual specimens under test. The tuned circuit and amplifier constitute an oscillator functioning at the frequency ($f0'$, FIG. 5) at which the overall phase shift is zero. When setting up the unit an operator adjusts the gain of the amplifier, and hence the voltage amplitude of the oscillator to a desired value, and thereafter the apparatus functions as described above with reference to FIG. 6.

Transistors TR3 and TR4 with their associated components form an integration or summation circuit (reference 3, FIG. 2) applying an output voltage at collector connection of TR4 inversely proportional to the amplitude of the output voltage of the oscillator, so that when the probe encounters a crack the voltage at collector connection of TR4 increases.

The threshold detector or discrimination circuit in the converter 3 referred to above, is represented by transistors TR6 and TR9, a conventional integrated circuit IC1, with their associated components. The resistors R16 and R17 provide a reference voltage for the second pin of the circuit IC1 and base connection of transistor TR6.

When the unit is correctly set up with the probe in the vicinity of unflawed metal the voltage at non-inverting input pin 3 of the circuit IC1 is equal to the voltage at inverting input pin 2 of the same circuit, and, by virtue of the characteristics of the circuit IC1, the voltage at output pin 6 of the same circuit is also of the same value as that at pins 2 and 3. Thus the voltage at the base connection of transistor TR9 is at the same value as that of transistor TR6. Thus in these circumstances no voltage is developed across resistor R23 and no current flows through transistor TR9 and resistor R27.

When the probe 1 encounters a crack the value of voltage applied to pin 3 of circuit IC1 is increased, and hence the value of the voltage at pin 6 of the same circuit is increased in linear relationship therewith. In consequence an increased voltage develops across the resistor R23, and the value of current flowing through transistor TR9 and resistor 23 is proportionately increased. This current develops a voltage across resistor R27, which determines the current flowing through the meter 5.

Any decrease in voltage at the pin 3 of circuit IC1 (due, for example, to removal of the probe from a metal object, or to the probe reaching the edge of specimen) causes a corresponding decrease in voltage at the pin 6 of circuit IC1, but this change of voltage is of the wrong polarity to cause flow of current through transistor TR9, and no indication is presented on the meter 5. Thus it will be seen that indications on the meter represent cracks, and have values directly proportional to the depths of cracks, with the range for which the meter is calibrated.

The abovementioned audio facility is provided by the circuit shown in the lower part of FIG. 7 connected to the resistor R14, and passing signals to earphones 7, with volume control provided by a variable resistor R38, and a variable threshold limiting resistor R25.

From the above description it will be seen that the invention provides a useful, linear-reading crack detector for metal specimens, but it should be understood that the invention is not limited solely to the details of the form described above, which may be modified, in order to meet various conditions and requirements encountered, without departing from the scope of the invention.

What we claim is:

1. In a device for detecting flaws in a surface of the kind having a detector coil for responding to variations in eddy currents induced in said surface; an oscillator circuit for establishing an oscillatory electromagnetic field at said coil and generating an output signal varying with the impedance of said coil; and means actuated by said output signal to provide an indicator signal which is substantially in linear proportion to a dimension of the flaw for the purpose of actuating indicating or measuring means to identify the flaw, the improvement consisting in that the oscillator circuit includes:

a tuned detector circuit comprising said detector coil, an inductor in series with said tuned circuit, a two-stage amplifier with adjustable gain, connected to said inductor, a feedback circuit maintaining zero phase shift between the said amplifier stages, and a capacitor providing capacitive reactance between the output of the amplifier and earth, means to adjust the oscillator so that the amplitude of the output signal decreases successively when the detector coil is moved from free air to adjacent a flawless part of the surface and then adjacent a flaw in the surface, said actuated means including a discriminator circuit whose discrimination level is set to pass only those oscillator signals whose amplitudes are less than or about equal to the amplitude of the output signal when the detector is adjacent a flawless part of the surface.

2. The device according to claim 1 in which the tuned circuit includes a capacitor in parallel with the detector coil.

3. The device according to claim 2 in which another capacitor is in parallel with the detector coil and inductor.

4. The device according to claim 3 which also comprises a converter circuit, connected between said oscillator output and the discriminator circuit, including AC to DC converter means to convert the oscillator output to a DC output having a voltage directly proportional to the amplitude of said oscillator output.

5. The device according to claim 4 wherein said converter circuit also includes inverting amplifier means to convert said DC output to a second DC output inversely proportional to the amplitude of the oscillator output.

6. The device according to claim 1 wherein a probe in the form of a tubular casing houses the components of the tuned detector circuit.

7. The device according to claim 4 wherein the converter circuit includes integrating means to integrate the variations of individual oscillations of the oscillator output over a pre-arranged short period of time.

8. A detector as claimed in claim 7 comprising an indicating or measuring device connected to said converter circuit and responsive to the value of the output signal provided by the converter circuit.

9. A detector as claimed in claim 7 comprising means for providing an audio signal controlled by and proportional to the output of said converter circuit.

10. A detector as claimed in claim 9 comprising an audio-generator incorporating threshold control, adapted to deliver an audible signal when the voltage supplied to the audio-generator from the converter circuit exceeds a pre-arranged threshold value.

11. A detector as claimed in claim 10 wherein the audiogenerator is adapted to provide an output signal of frequency which varies with, and in proportion to, the value of the voltage applied thereto above the threshold value.

* * * * *